(12) United States Patent
Vaillancourt

(10) Patent No.: US 7,004,934 B2
(45) Date of Patent: Feb. 28, 2006

(54) CLOSED SYSTEM CONNECTOR ASSEMBLY

(76) Inventor: Vincent L. Vaillancourt, 14 Bunyan Dr., Livingston, NJ (US) 07039

( * ) Notice: Subject to any disclaimer, the term of this patent is extended or adjusted under 35 U.S.C. 154(b) by 113 days.

(21) Appl. No.: 10/236,147

(22) Filed: Sep. 6, 2002

(65) Prior Publication Data

US 2003/0060804 A1 Mar. 27, 2003

Related U.S. Application Data

(60) Provisional application No. 60/317,143, filed on Sep. 6, 2001.

(51) Int. Cl.
*A61M 15/16* (2006.01)
*A61M 25/18* (2006.01)
*A61M 39/00* (2006.01)
*A61M 39/10* (2006.01)

(52) U.S. Cl. .............. 604/533; 604/167.02; 37/164.01; 37/164.02

(58) Field of Classification Search ......... 604/533–539, 604/513, 99.04, 167.01–167.04, 905; 137/614, 137/614.01–614.05; 251/149, 149.1–149.7
See application file for complete search history.

(56) References Cited

U.S. PATENT DOCUMENTS 3,986,508 A * 10/1976 Barrington ................. 604/411
5,122,123 A * 6/1992 Vaillancourt ................ 604/192
5,474,536 A * 12/1995 Bonaldo ...................... 604/86
5,487,728 A * 1/1996 Vaillancourt ................ 604/86
5,492,147 A * 2/1996 Challender et al. .... 137/614.05
5,509,912 A * 4/1996 Vaillancourt et al. ....... 604/537
5,514,116 A * 5/1996 Vaillancourt et al. ....... 604/537
5,669,891 A * 9/1997 Vaillancourt ................ 604/537
5,848,997 A * 12/1998 Erskine et al. ............. 604/533
6,050,978 A * 4/2000 Orr et al. .................... 604/249
6,273,869 B1 * 8/2001 Vaillancourt ................ 604/86
2003/0032940 A1 * 2/2003 Doyle ......................... 604/533
2003/0120221 A1 * 6/2003 Vaillancourt ................ 604/256

* cited by examiner

*Primary Examiner*—Nicholas D. Lucchesi
*Assistant Examiner*—Catherine S. Williams
(74) *Attorney, Agent, or Firm*—Francis C. Hand; Carella, Byrne, Bain et al.

(57) ABSTRACT

A male adaptor is provided with a nose for penetrating into a housing of the female connector. A septum is disposed over the nose of the male adaptor to maintain a seal with the female connector during coupling and uncoupling. Upon coupling, the septum dilates to allow the nose to pass through. The female connector may have a septum that also dilates to allow penetration of the nose of the male adaptor. Alternatively, the septum of the female connector may be retractable under the force of the nose of the male adaptor.

15 Claims, 4 Drawing Sheets

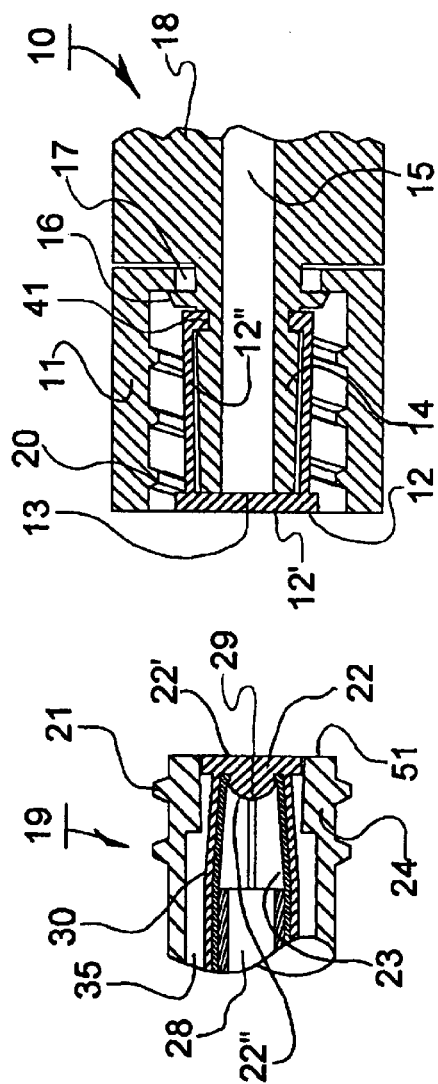
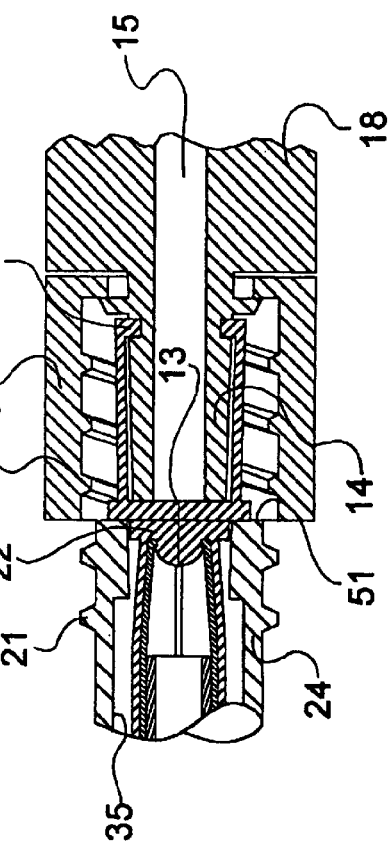
FIG. 1
FIG. 2
FIG. 3

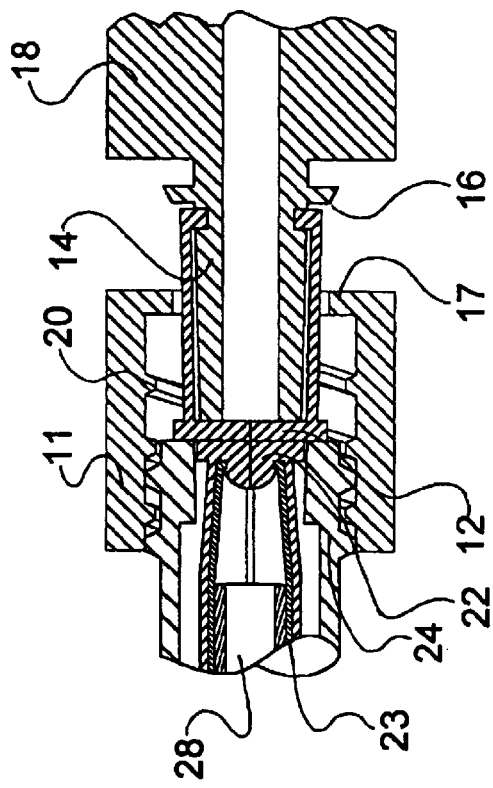
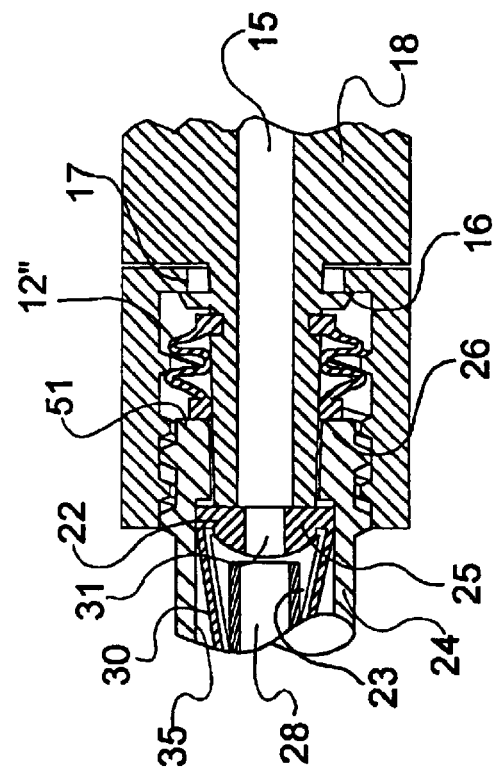

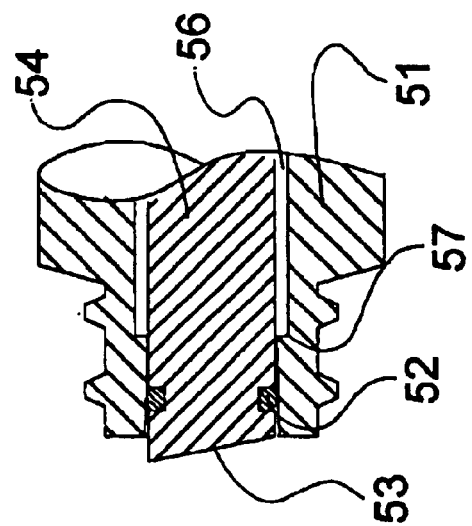
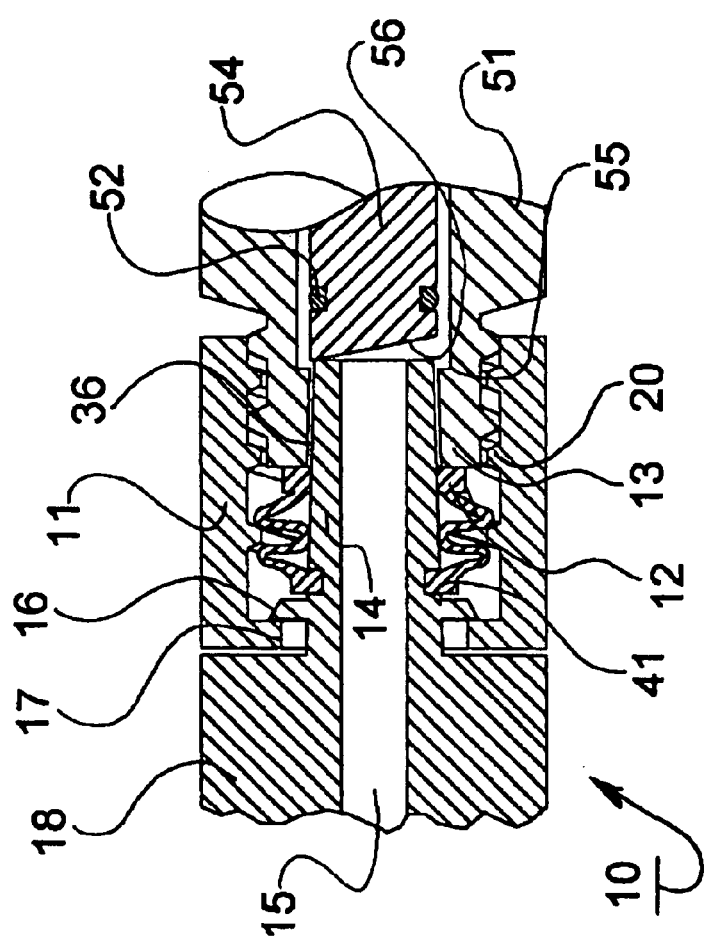

CLOSED SYSTEM CONNECTOR ASSEMBLY

This application claims the priority benefit of Provisional Patent Application No. 60/317,143 filed Sep. 6, 2001.

This invention relates to a closed system connector assembly. More particularly, this invention relates to a closed system connector assembly having a swabable male adaptor and a swabable female connector for use particularly in the health care industry.

As is known, the health care industry is concerned with microorganisms, such as bacteria and the like, which may cause health problems. In some cases, people become patients because these microorganisms become unmanageable and threaten or endanger the health of the patient.

Patients requiring therapy are often placed in a position where their normal defenses against microorganisms are compromised. As a result, the patients may develop nosocomal infections while being treated for another disease during therapy. As has been recognized, a major cause of nosoicomal infections has been due to the connection/disconnection of tubing lines, especially in the area of IV therapy. This is one of the reasons why most IV Administration Sets (IV tubing with connectors) are discarded every forty-eight to seventy two hours.

In the development of connectors for tubing lines, primary concern has generally been with having a connector which can readily be closed and sealed and just as readily be opened with a minimum of force. A so-called luer connection is the generally accepted standard for the health care industry. This connector is easy to open and close and requires little force while at the same time providing a positive seal. However, one disadvantage of this connector is that after fluid flows through a connection made by the connector, if the user wishes to open the connection and then reconnect the connection, the chance of microorganism contamination is sufficiently large that most hospitals do not allow this practice except under abnormal circumstances.

In order to provide a system, which can be connected, for the transfer of medication, followed by a sterile disconnection, the use of a Y-site connector has been developed. In this case, the connection is in the form of a plastic fitting having one end covered with a rubber septum. In order to deliver fluid into the connector, a sterile needle pierces through the rubber septum in order to transfer fluid into the line to which the connection is connected. After fluid transfer is completed, the needle is removed and the rubber septum self closes to maintain what is commonly referred to as a closed system and sterility of the line is maintained. Everything associated with the now removed needle is considered to be non-sterile since the exit port of the needle is exposed to the atmosphere and almost immediately becomes contaminated.

U.S. Pat. No. 5,122,123 describes a product, which has membranes on both parts of the connection assembly. One part further contains a cannula, which has about it a membrane, which is collapsible. Upon joining the two portions of the connector together, the one membrane collapses as the cannula enters the other portion of the connector thereby opening the septum and providing for a continuous passage for fluid flow. Upon disconnect, the cannula is resheathed within the membrane prior to removal thereby maintaining a sterile path within both portions of the connector assembly. This assembly requires two connector halves, which are uniquely designed to mate with each other. As a result, existing connector products are generally not viable when a connector half does not contain a membrane or the membrane opens when the central portion of the connector is forced inward by the action of a male luer adaptor.

Accordingly, it is an object of this invention to provide a connector assembly, which can be readily made sterile on site immediately prior to forming a connection.

It is another object of this invention to provide a connector, which can be used with existing available connectors to achieve a sterile connection/disconnection.

Briefly, the invention provides a closed system connector assembly comprising a male adaptor attached to a female connector. The female connector may be a needleless type generically described as a pressure opening swabable valve that opens upon the attachment of a male luer connector portion. Swabable valves of the needleless type include the CLC 2000 made by ICU Medical, POSIFLOW, made by Becton Dickinson. Other valves of this type are made by B. Braun and Kippmed to name a few.

The male adaptor of this invention is constructed with a tubular portion to define a lumen and a membrane or septum at one end of the tubular portion for sealing the lumen.

The female connector to which the male adaptor connects has a housing defining a lumen and a membrane or equivalent surface that may be swabbed to achieve a sterile interface for sealing the lumen and for abutting the membrane of the male connector.

Upon movement of the male adaptor against the female connector swabable face (membrane), the membrane covering the nose of the male adaptor is opened exposing the tubular lumen which enters the female connector housing. As the nose portion moves into a housing of the female connector, the female connector housing lumen is opened to provide fluid communication between the connectors. The face portion of the male adaptor membrane engages the flange or face of the female connector housing forming a seal between the two connectors with the outside environment. Upon uncoupling, the female connector closes prior to removal of the nose portion of the male adaptor. As the male adaptor disengages from the female connector, the septum closes prior to the exposure of the male lumen to the environment thereby maintaining a sterile fluid path in both the male adaptor and the female connector.

In this manner, a sterile connection is achieved with an existing needleless pressure opening connector which is swabable to achieve sterility at the face prior to use. The closed system connector allows a sterile connection to be achieved many times by simply swabbing both system connector halves prior to connection.

In another embodiment, the female connector may include a hollow needle disposed within the lumen that is positioned for entry into the lumen of the male adaptor.

These and other objects and advantages of the invention will become more apparent from the following detailed description taken in conjunction with the accompanying drawings wherein:

FIG. 1 illustrates a cross-sectional view of the male adaptor portion of a closed system connector constructed in accordance with the invention with a reseal member thereof in a first, closed position;

FIG. 2 illustrates a cross sectional partial view of a commercial needleless connector;

FIG. 3 illustrates a cross sectional view of the male adaptor of FIG. 1 in abutment with the female connector of FIG. 2;

FIG. 4 illustrates a cross sectional view of the male adaptor of FIG. 1 penetrating the female connector of FIG. 2;

FIG. 5 illustrates a cross sectional view similar to FIG. 4 with of a portion of the swabable membrane of the male adaptor opened and pushed up the housing of the male adaptor.

FIG. 6 illustrates s a cross sectional view of a portion of a swabable valve which has a central mandrel;

FIG. 7 is a cross sectional view of the swabable valve of FIG. 6 connected to the tubular portion of the male adaptor of FIG. 1;

DETAILED DESCRIPTION OF THE PREFERRED EMBODIMENT

Figure 8:
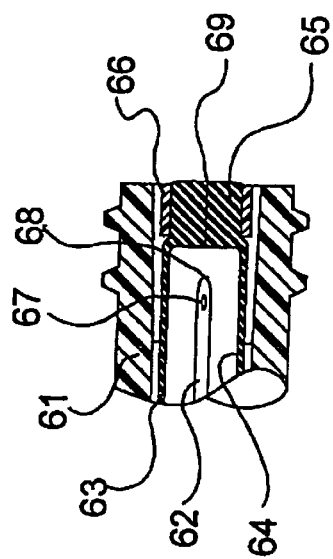
FIG. 8 illustrates a cross-sectional view of needle containing female connector.

Referring to FIG. 1, the male adaptor 10 includes a housing 18 having a projecting nose or tubular portion 14 and a passage or lumen 15 that extends centrally therethrough. As illustrated the outer surface of the nose 14 is tapered downwardly towards the forward end.

In addition, the adaptor 10 has a locking ring 11 mounted concentrically of the nose 14 that is provided with an internal thread 20. The locking ring 11 is locked in place on the nose 14 by the relative dimensions of an integral ring 16 on the nose 14 and an internal ring or collar 17 on the end of the locking ring 11. The ring 16 has a greater outside diameter than the inside diameter of the ring 17 to create an interference fit preventing the locking ring 11 from moving along the nose 14. The locking ring 11 in this embodiment is free to rotate about the axis of the nose 14.

A septum or membrane 12 is mounted on the nose 14 to close over the passage 15. This septum 12 includes a disk-shaped body 12' sealing over the passage 15 and a tubular sleeve 12" that extends over the nose 14. The disk-shaped body 12' has a flat swabable surface coincident, i.e. flush, with the end of the locking ring 11. As such, the face of the septum 12 can be easily swabbed prior to use.

As illustrated, the septum 12 has an internal flange at one end that fits into an annular groove 41 in the nose 14 to secure the septum 12 in place. In addition, the septum 12 has a weakened section 13, such as a slit or pierced point, centrally of the disk-shaped body 12' that is in line with the passage or lumen 15.

The housing 18 is typically sterilized and may be connected to a tubing or have an end connector (not shown) for attachment to a fluid source for administration.

Referring to FIG. 2, the female connector 19 is in the form of a needleless injection site. As indicated, the female connector 19 includes a hollow housing 24 with an external thread 21 for threading of the locking ring 11 thereon (see FIG. 5). As indicated in FIG. 5, the forward end of the housing 24 has an internal wall that is tapered to receive the tapered nose 14 of the male adaptor 10.

In addition, the female connector 19 has a centrally disposed tubular member 28 disposed concentrically within the housing 24 to define a passage or lumen therethrough. The tubular member 28 carries a segmented sleeve 23 that is slidably mounted thereon under the bias of a spring (not shown) to move from a retracted position, as shown in FIG. 5, to an extended position, as shown in FIG. 2. The sleeve 23 is formed with a plurality of leaf spring-like elements that project beyond the tubular member 28 and that are bent or angled radially inwardly for purposes as described below.

A septum or membrane 22 is mounted on the segmented sleeve 23 to seal off the lumen of the tubular member 28. As shown, the septum 22 has a flat disk-like body 22' with a flat face at the entry to the housing 24, a bulbous portion 22" extending into the segmented sleeve 23 and a tubular sleeve 30 fitted over the segmented sleeve 23 and secured thereto in a suitable manner. The flat face of the body 22' of the septum 22 is coincident, i.e. flush, with a face 51 of the housing 24 so as to be swabable prior to use. In addition, the flat body 22' of the septum 22 has slit 29 aligned with the passage in the tubular member 28.

As illustrated, the body 22' of the septum 22 is slidably received in the tapered forward end of the housing 24 and forms a seal thereat. In addition, the housing 24 has a recessed portion 35 of greater inside diameter than the forward portion to accommodate expansion of the segmented sleeve 23 as explained below.

Referring to FIG. 3, wherein like reference characters indicate like parts as above, prior to connecting the male adaptor 10 and the female connector 19, the respective septums 12, 22 of each component is swabbed for sterilization purposes. Next, the male adaptor 10 is brought up against the female connector 19. At this time, the septum 12 of the male adaptor 10 abuts against the septum 22 of the female connector 19 to maintain a sterile contact. At the same time, the outer periphery of the flat body 12' of the septum 12 abuts against the face 51 of the housing 24.

Next, the male adaptor 10 is pushed towards the female connector 19. At this time, the nose 14 of the male adaptor 10 being of less outside diameter than the inside diameter of the connector housing 24 causes the flat body 12' of the septum 12 to distort so that the slit 13 dilates to thereby open to allow penetration of the nose 14 into the housing 24 the female connector 19. At this time, the housing 24 of the female connector 19 pushes the dilated body 12' of the septum 12 along the nose 14 as indicated in FIG. 5 to a retracted position. In this position, the sleeve 12" of the septum 12 resiliently collapses into a bellows shape.

Further, as the nose 14 penetrates the housing 24 of the female connector 19, the septum 22 therein is pushed rearwardly into the recessed portion 35. At this time, the sleeve 23 is also pushed rearwardly so that the inwardly bent leaf spring elements of the segmented sleeve 23 expand radially outwardly as they pass over the end of the tubular member 28. This in turn, causes the slit 29 of the septum 22 to dilate to form a passage 31. In this way, the passage 15 of the male adaptor 10 comes into communication with the lumen of the tubular member 28 to allow fluid to pass therebetween.

Continued movement of the nose 14 into the connector 19 causes the leaf spring elements to flex further outwardly to the condition shown in FIG. 5 thereby further dilating the passage 31.

When the leaf spring elements of the segmented sleeve 23 are in the position illustrated in FIG. 3, the forward end of the housing 24 prevents outward flexing of the leaf spring elements.

As indicated in FIG. 5, the resiliently collapsed septum 12 maintains a seal tight fit against the face 51 of the housing 24 of the female connector during the connection process of the male adaptor 10 to the female connector 19.

Upon disconnecting the male adaptor 10 from the female connector 19, the nose 14 retracts from the body 22' of the septum 22. The leaf spring elements then flex inwardly causing the body 22' to circumferentially collapse to a diameter sufficient to allow passage of the body 22' into the forward end of the housing 24. Continued withdrawal of the nose 14 from the housing 24 allows the segmented sleeve 23 to be spring biased back to the extended position of FIG. 3. At this time, the leaf spring elements of the segmented sleeve 23 also collapse back into the position illustrated in FIG. 3 so that the septum body 22' closes and again seals against the inside wall of the housing 24 thereby maintaining the female connector 19 in a sterile condition.

As the nose 14 is being withdrawn from the housing 24 the female connector 19, the sleeve 12" of the septum 12 expands from the position of FIG. 5 towards the position indicated in FIG. 3 while remaining in sealing contact with the housing 24. As the nose 14 achieves the position shown in FIG. 3, the body 12' of the septum 12 closes over the passage 15 of the nose 14 while remaining in contact with the face 51 of the connector 24. This maintains the passage 15 of the male adaptor 10 in a sterile condition.

Referring to FIG. 4, wherein like reference characters indicate like parts as above, the locking ring 11 may be mounted over the nose 14 of the male adaptor without being locked thereon. In this embodiment, the locking ring 11 is free to move axially relative to the nose of the adaptor. Thus, the locking ring 11 may be threaded onto the female connector 24 before the nose 14 of the male adaptor is pushed into the housing 24 of the female connector.

The locking ring 11 may be mounted on the male adaptor and held in place by posts (not shown) on the housing 18 that align with key locks (not shown) on the internal flange of the locking ring 11. When the posts align with the key lock, the locking ring 11 may be moved axially relative to the housing 18.

Referring to FIG. 6, the female connector may be constructed with a housing 51 having an external thread within which a mandrel 54 is slideably mounted. As indicated, the mandrel 54 has an inclined face 53 and is sealed relative to the forward end of the housing 51 by a sealing ring 52. In addition, the housing 51 is provided with a recess 57 in order to form an annular space or gap between the housing 51 and the mandrel 54 for the passage of fluid.

Referring to FIG. 7, wherein like reference characters indicate like parts as above, as the tapered nose 14 of the male adaptor 10 is pushed into the housing 51 of the connector, the mandrel 54 is pushed backwardly in order to expose the annular gap between the housing 51 and the mandrel 54 to the passage 15 in the male adaptor 10. As above, the septum 12 on the male adaptor 10 moves up the tapered nose 14 thereby opening the septum 12 while maintaining a seal between the septum 12 and the face of the housing 51.

Referring to FIG. 8, the female connector may be constructed with a tubular housing 61 having an external thread and a hollow needle 62 disposed concentrically within the housing 61. In addition, a tubular member 63 is disposed concentrically between the housing 61 and the needle 62 to define a passage 64 therethrough. In addition, a septum 65 is formed integrally with the tubular member 63 to seal off the passage 64. This septum 65 also has a centrally disposed slit 69 and a ring 66 disposed circumferentially of the septum 65 to maintain a compressive force on the slit 69 to maintain the slit 69 closed.

Figure 9:
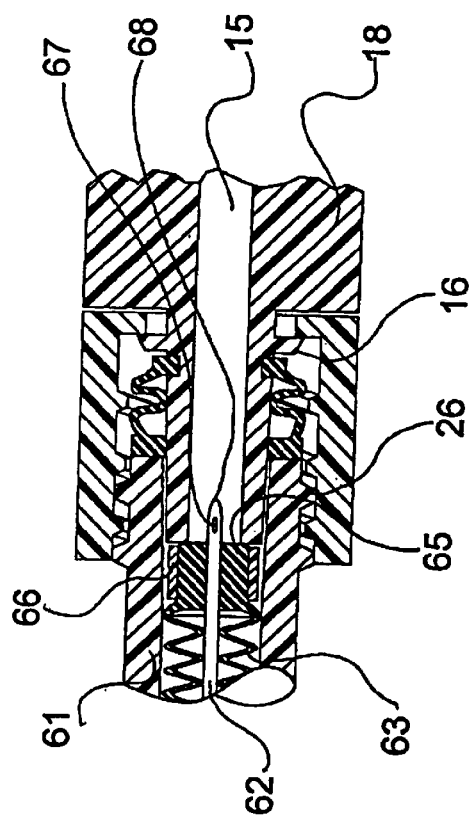
FIG. 9 illustrates a cross-sectional view of the female connector of FIG. 8 connected to a male adaptor of FIG. 1.

Referring to FIG. 9, wherein like reference characters indicate like parts as above, when the male adaptor is inserted into the connector of FIG. 8, the septum 65 is pushed backwardly from the position shown in FIG. 8 to allow the needle 62 to pass through the slit 69 of the septum 65. To this end, the needle has an opening 67 in a side wall and a blunt end 68 to avoid coring of the septum 69.

As shown in FIG. 9, the tubular member 63 collapses resiliently into a bellows shape. Upon retraction of the male adaptor, the tubular portion 63 springs back into the condition illustrated in FIG. 8 to allow the septum 65 to again seal off the passage 64.

The invention thus provides a male adaptor which is able to maintain a sealed passageway for fluids during coupling with and uncoupling from a female connector.

Further, the invention provides a closed system connector assembly wherein a male adaptor and a female connector may be readily made sterile on site immediately prior to performing a connection and maintained sterile after disconnection.

What is claimed is:

1. A closed system connector assembly comprising
a male adaptor including a first housing having a projecting nose and a passage extending centrally therethrough, a locking ring mounted concentrically about said nose, and a first septum mounted on said nose and including a disk shaped body sealing over said passage and a tubular sleeve extending over said nose, said disk shaped body having a swabable surface flush with an end of said locking ring; and
a female connector including a second housing having an external thread for threading into said locking ring of said male adaptor and being of an internal diameter to receive said nose of said male adaptor therein, a tubular member disposed concentrically within said second housing and defining a passage therethrough, and a second septum mounted on said tubular member and having a swabable surface flush with an end of said second housing.

2. A closed system connector assembly as set forth in claim 1 wherein said first septum includes a centrally disposed slit whereby upon penetration of said nose of said male adaptor into said second housing of said female connector, said body of said first septum dilates about said nose and said housing of said female connector pushes said dilated body along said nose to a retracted position.

3. A closed system connector assembly as set forth in claim 2 wherein said tubular sleeve of said first septum is resiliently collapsible during movement of said dilated body along said nose to a said retracted position whereby upon removal of said nose from said female connector said sleeve extends to return said dilated body over said passage in said tubular member.

4. A closed system connector assembly as set forth in claim 3 wherein said tubular sleeve of said first septum includes an internal flange at one end and said nose has an annular groove receiving said flange therein.

5. A closed system connector assembly as set forth in claim 1 wherein said female connector includes a segmented sleeve mounted on and projecting from said tubular member, said segmented sleeve having said second septum mounted thereon.

6. A closed system connector as set forth in claim 5 wherein said second septum has a bulbous portion extending into said segmented sleeve and a centrally disposed slit in said bulbous portion.

7. A closed system connector as set forth in claim 1 wherein said second septum has a slit disposed centrally thereof.

8. A closed system connector assembly comprising
a male adaptor including a first housing having a projecting nose and a passage extending centrally therethrough, a locking ring mounted concentrically about said nose, and a first septum mounted on said nose and including a disk shaped body sealing over said passage and a tubular sleeve extending over said nose, said disk shaped body having a swabable surface coplanar with an end of said locking ring; and
a female connector including a tubular housing for securement within a said locking ring of said male adaptor and having an internal diameter to receive a said nose of said male adaptor therein, a tubular member disposed concentrically within said tubular housing and defining a passage therethrough, and a second septum mounted on said tubular member and having a swabable surface coplanar with an end of said tubular housing.

9. A closed system connector assembly as set forth in claim 8 wherein said first septum includes a centrally disposed slit whereby upon penetration of said nose of said male adaptor into said tubular housing of said female connector, said body of said first septum dilates about said nose and said tubular housing of said female connector pushes said dilated body along said nose to a retracted position.

10. A closed system connector assembly as set forth in claim 9 wherein said tubular sleeve of said first septum is resiliently collapsible during movement of said dilated body along said nose to said retracted position whereby upon removal of said nose from said female connector said sleeve extends to return said dilated body over said passage in said tubular member.

11. A closed system connector assembly as set forth in claim 10 wherein said tubular sleeve of said first septum includes an internal flange at one end and said nose has an annular groove receiving said flange therein.

12. A closed system connector assembly as set forth in claim 8 wherein said female connector includes a segmented sleeve mounted on and projecting from said tubular member, said segmented sleeve having said second septum mounted thereon.

13. A closed system connector as set forth in claim 12 wherein said second septum has a bulbous portion extending into said segmented sleeve and a centrally disposed slit in said bulbous portion.

14. A closed system connector as set forth in claim 8 wherein said female connector includes a hollow needle disposed concentrically in said tubular member and said second septum is disposed in one end of said tubular member.

15. A closed system connector as set forth in claim 14 wherein said second septum has a silt disposed centrally thereof.

* * * * *

UNITED STATES PATENT AND TRADEMARK OFFICE
CERTIFICATE OF CORRECTION

PATENT NO.    : 7,004,934 B2
DATED         : February 28, 2006
INVENTOR(S)   : Vincent L. Vaillancourt It is certified that error appears in the above-identified patent and that said Letters Patent is hereby corrected as shown below:

Column 6,
Line 37, "to a said" should be -- to said --.

Signed and Sealed this

Eighteenth Day of April, 2006

JON W. DUDAS
*Director of the United States Patent and Trademark Office*